US012672978B2

(12) United States Patent
Tran

(10) Patent No.: US 12,672,978 B2
(45) Date of Patent: Jul. 7, 2026

(54) MENSTRUAL RECEPTACLE APPLICATOR AND METHOD OF INSERTING A MENSTRUAL RECEPTACLE

(71) Applicant: Cleva LLC, Des Moines, IA (US)

(72) Inventor: Christine Tran, Des Moines, IA (US)

(73) Assignee: Cleva LLC, Des Moines, IA (US)

( * ) Notice: Subject to any disclaimer, the term of this patent is extended or adjusted under 35 U.S.C. 154(b) by 910 days.

(21) Appl. No.: 17/930,630

(22) Filed: Sep. 8, 2022

(65) Prior Publication Data

US 2023/0091123 A1     Mar. 23, 2023

Related U.S. Application Data

(60) Provisional application No. 63/261,032, filed on Sep. 9, 2021.

(51) Int. Cl.
    *A61F 5/455*        (2006.01)
    *A61F 6/12*         (2006.01)
(52) U.S. Cl.
    CPC ............ *A61F 5/4553* (2013.01); *A61F 5/455* (2013.01); *A61F 6/12* (2013.01)
(58) Field of Classification Search
    CPC ........... A61F 5/4553; A61F 5/455; A61F 6/12
    See application file for complete search history.

(56) References Cited

U.S. PATENT DOCUMENTS 6,332,878 B1 * 12/2001 Wray .................... A61F 5/4556
                                                    128/830
6,582,389 B2 * 6/2003 Buzot ..................... A61F 13/26
                                                    604/11

(Continued)

FOREIGN PATENT DOCUMENTS

CN     109833136  A    6/2019
KR     200486704  Y1   7/2018

OTHER PUBLICATIONS https://sunnyperiod.com/ home page access on Jul. 8, 2022, 13 pps.

*Primary Examiner* — Guy K Townsend
(74) *Attorney, Agent, or Firm* — McKee, Voorhees & Sease, PLC

(57) ABSTRACT

The present disclosure provides a menstrual receptacle applicator. The applicator includes a hollow cylindrical main body defining an open proximal end and an open distal end, the main body having an inner diameter of 16 millimeters (mm) to 30 mm at the proximal end and configured to house at least a portion of a menstrual receptacle. The menstrual receptacle applicator further comprises a push rod dimensioned to be inserted into and reciprocally moved within the main body. A kit is also provided, including one or more menstrual receptacles and a menstrual receptacle applicator. Further, a method of inserting a menstrual receptacle is provided. The method includes a) obtaining a menstrual receptacle applicator; either i) rolling the menstrual receptacle into a spiral to form a rolled menstrual receptacle or ii) flattening the receptacle to form a compacted menstrual receptacle; and b) at least partially inserting the rolled menstrual receptacle or the compacted menstrual receptacle into the proximal end of the main body. The method further comprises c) inserting a proximal end of the push rod into the distal end of the main body; d) inserting the proximal end of the main body containing the rolled menstrual receptacle or the compacted menstrual receptacle into a vaginal opening; and e) pushing the push rod toward the proximal end of the main body until the proximal end of the push rod pushes the rolled menstrual receptacle or the compacted menstrual receptacle into the vaginal opening.

16 Claims, 12 Drawing Sheets

(56)     References Cited

U.S. PATENT DOCUMENTS

|                   |       |         |                                |
| ----------------- | ----- | ------- | ------------------------------ |
| D719,653          | S     | 12/2014 | Agrawal                        |
| 11,369,509        | B2 *  | 6/2022  | Garriga I Rodo .... A61F 5/4553 |
| 2002/0111578      | A1 *  | 8/2002  | Buzot ..................... A61F 13/26 |
|                   |       |         | 604/14                         |
| 2009/0247930      | A1 *  | 10/2009 | Fung ..................... A61F 13/266 |
|                   |       |         | 604/16                         |
| 2019/0083296      | A1 *  | 3/2019  | Miller ................... A61F 5/4553 |
| 2019/0151136      | A1 *  | 5/2019  | Garriga I Rodo ...... A61F 13/15 |
| 2022/0378627      | A1 *  | 12/2022 | Agbo .................... A61F 5/4553 |
| 2023/0019578      | A1 *  | 1/2023  | Belardo ................ A61F 5/4553 |
| 2023/0091123      | A1 *  | 3/2023  | Tran ..................... A61F 5/4553 |
|                   |       |         | 604/330                        |

* cited by examiner

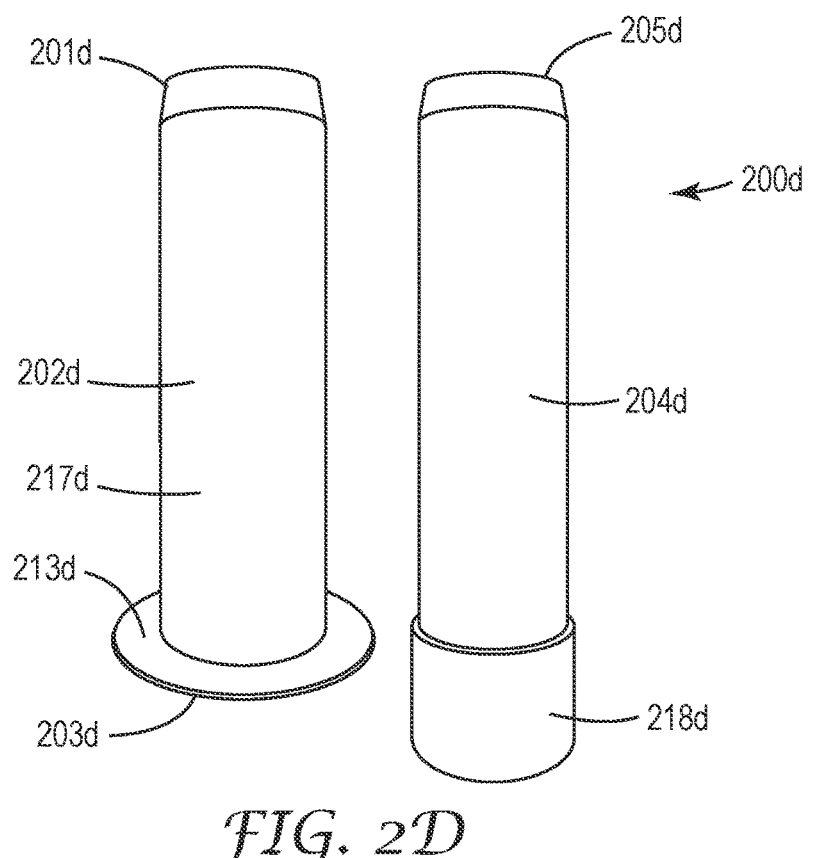
*FIG. 2D*
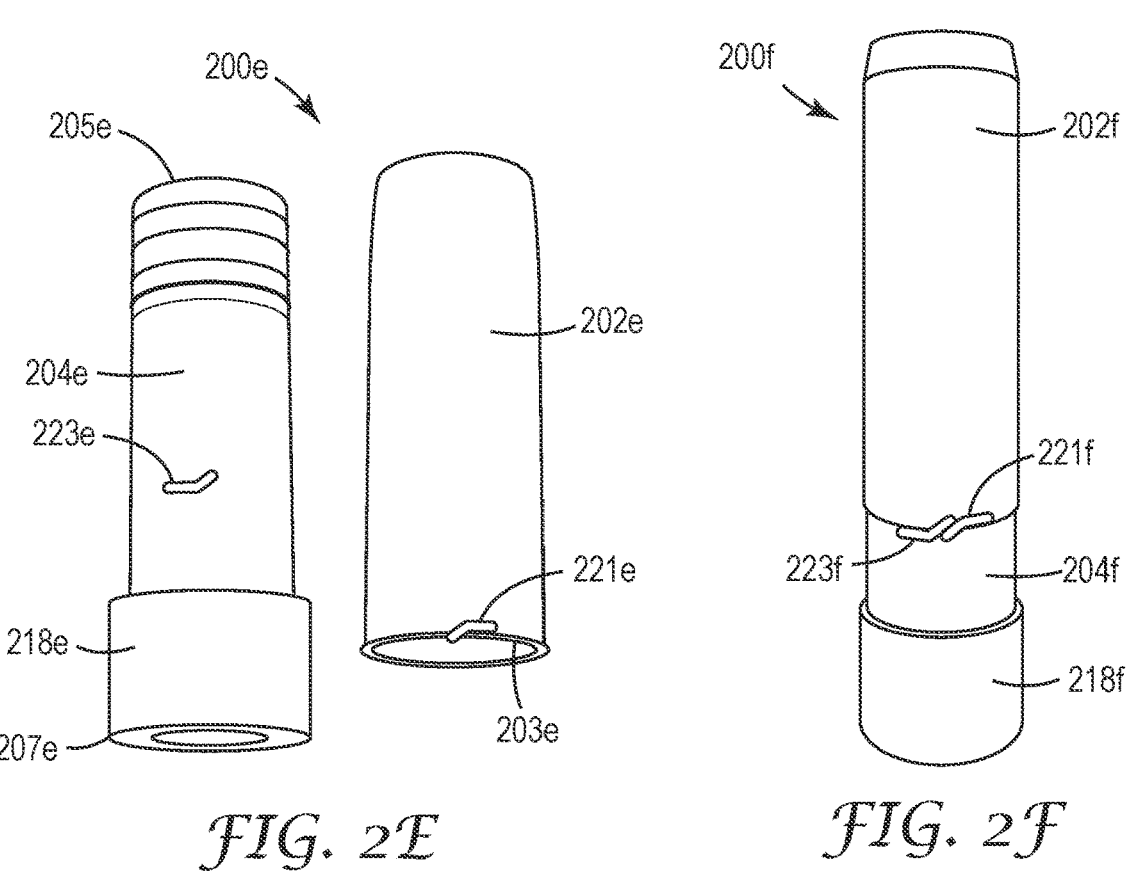
*FIG. 2E*        *FIG. 2F*

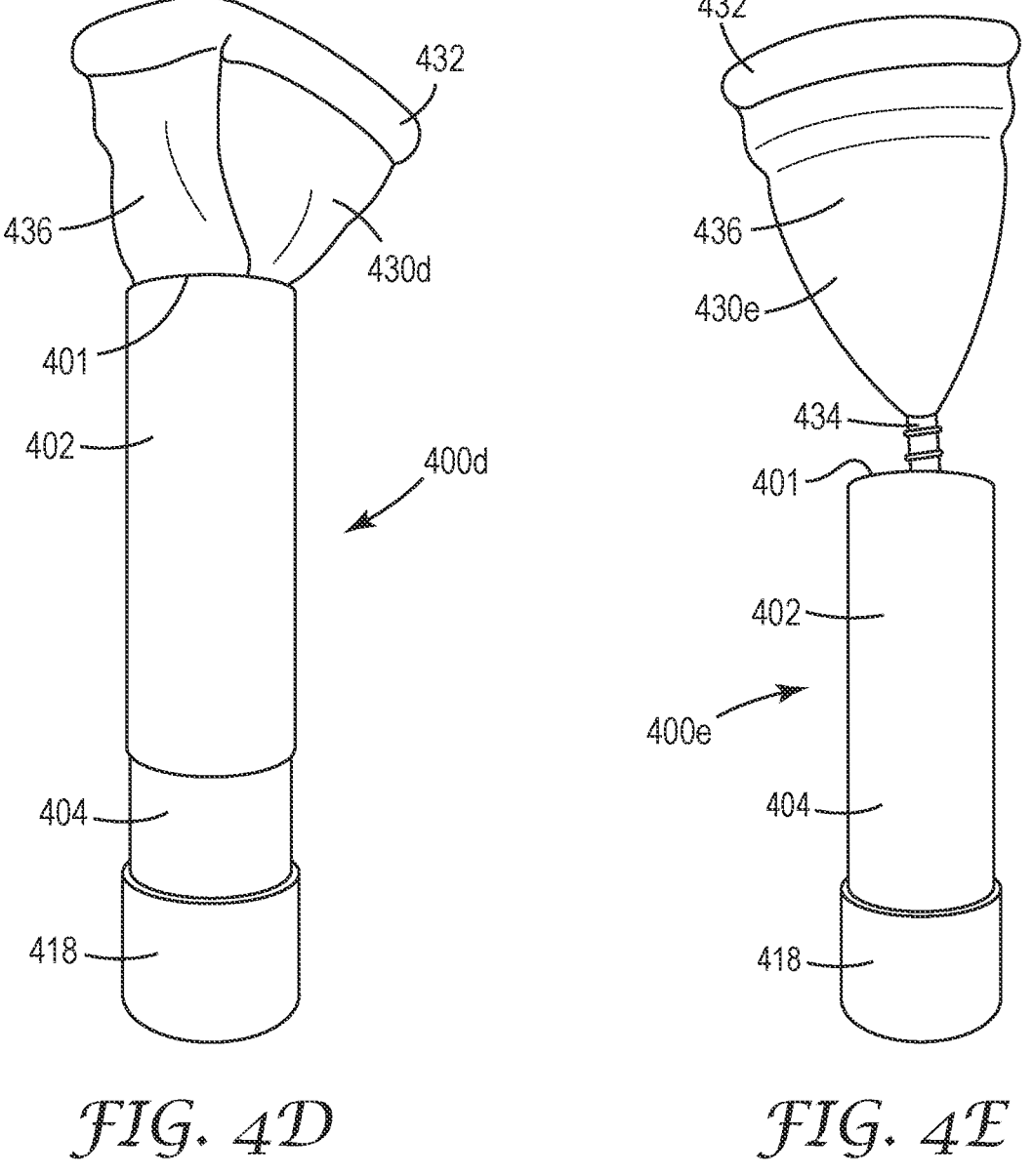
*FIG. 4D* *FIG. 4E*

650a

652

652

650b

656

654

756

752

750

754 a) Obtain a menstrual receptacle applicator comprising:

Figure 9:
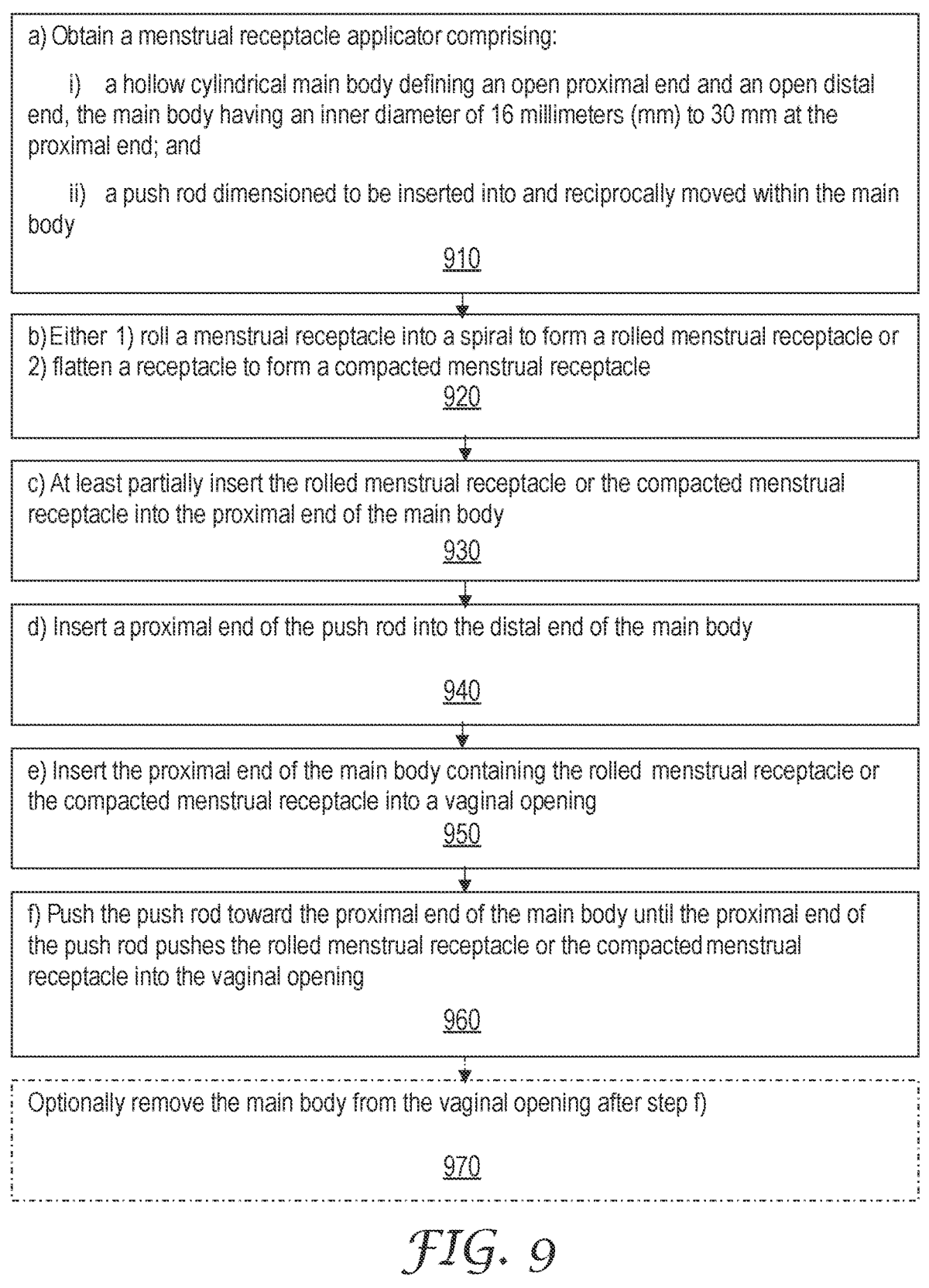

i)   a hollow cylindrical main body defining an open proximal end and an open distal end, the main body having an inner diameter of 16 millimeters (mm) to 30 mm at the proximal end; and ii)   a push rod dimensioned to be inserted into and reciprocally moved within the main body

910

↓ b) Either 1) roll a menstrual receptacle into a spiral to form a rolled menstrual receptacle or 2) flatten a receptacle to form a compacted menstrual receptacle

920

↓ c) At least partially insert the rolled menstrual receptacle or the compacted menstrual receptacle into the proximal end of the main body

930

↓ d) Insert a proximal end of the push rod into the distal end of the main body

940

↓ e) Insert the proximal end of the main body containing the rolled menstrual receptacle or the compacted menstrual receptacle into a vaginal opening

950

↓ f) Push the push rod toward the proximal end of the main body until the proximal end of the push rod pushes the rolled menstrual receptacle or the compacted menstrual receptacle into the vaginal opening

960

↓

Optionally remove the main body from the vaginal opening after step f)

MENSTRUAL RECEPTACLE APPLICATOR AND METHOD OF INSERTING A MENSTRUAL RECEPTACLE

TECHNICAL FIELD

The present disclosure relates to applicators for menstrual receptacles (e.g., cups, discs, etc.) and methods of inserting the menstrual receptacles.

BACKGROUND

Menstrual receptacles, for instance menstrual cups and menstrual discs, which collect a volume of fluid during use in a non-absorbent vessel, provide certain advantages over absorbent menstrual products such as sanitary napkins and tampons. Such advantages include, for example, being more environmentally friendly and/or cost-effective due to typically being reusable, as well as decreasing at least one of odor, leakage, or risk of adverse health issues (e.g., dehydration, toxic shock syndrome, etc.). To increase the utilization of menstrual receptacles, there remains a need for greater ease in their application.

SUMMARY

The present disclosure provides menstrual receptacle applicators, kits, and methods of inserting menstrual receptacles.

In a first aspect, a menstrual receptacle applicator is provided. The menstrual receptacle applicator comprises a hollow cylindrical main body defining an open proximal end and an open distal end, the main body having an inner diameter of 16 millimeters (mm) to 30 mm at the proximal end and configured to house at least a portion of a menstrual receptacle. The menstrual receptacle applicator further comprises a push rod dimensioned to be inserted into and reciprocally moved within the main body.

In a second aspect, a kit is provided. The kit comprises one or more menstrual receptacles; and the menstrual receptacle applicator according to the first aspect.

In a third aspect, a method of inserting a menstrual receptacle is provided. The method comprises a) obtaining a menstrual receptacle applicator; either 1) rolling a menstrual receptacle into a spiral to form a rolled menstrual receptacle or 2) flattening a receptacle to form a compacted menstrual receptacle; and b) at least partially inserting the rolled menstrual receptacle or the compacted menstrual receptacle into the proximal end of the main body. The method further comprises c) inserting a proximal end of the push rod into the distal end of the main body; d) inserting the proximal end of the main body containing the rolled menstrual receptacle or the compacted menstrual receptacle into a vaginal opening; and e) pushing the push rod toward the proximal end of the main body until the proximal end of the push rod pushes the rolled menstrual receptacle or the compacted menstrual receptacle into the vaginal opening. The menstrual receptacle applicator comprises a hollow cylindrical main body defining an open proximal end and an open distal end, the main body having an inner diameter of 16 millimeters (mm) to 30 mm at the proximal end; and a push rod dimensioned to be inserted into and reciprocally moved within the main body.

Various unexpected results and advantages are obtained in exemplary embodiments of the disclosure. One such advantage of exemplary embodiments of the present disclosure is the provision of a simple and effective menstrual receptacle applicator and its use in inserting a menstrual receptacle.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the cited list serves only as a representative group and should not be interpreted as an exclusive list.

BRIEF DESCRIPTION OF THE DRAWINGS

FIG. 2d is a schematic perspective view of an exemplary menstrual receptacle applicator including a push rod and a main body sized to form a compression fit when the push rod is inserted into the main body.

FIG. 2e is a schematic perspective view of an exemplary menstrual receptacle applicator including a push rod and a main body, each comprising a portion of a clasp to engage when the push rod is partially inserted into the main body.

FIG. 2f is a schematic perspective view of the exemplary menstrual receptacle applicator of FIG. 2e assembled, with the two portions of the clasp engaged with each other.

FIG. 4a is a schematic top view of a rolled menstrual cup to be used in a menstrual receptacle applicator according to the present disclosure.

FIG. 4b is a schematic side view of the rolled menstrual cup of FIG. 4a.

FIG. 4c is a schematic perspective view of the rolled menstrual cup of FIGS. 4a-4b disposed partially into the proximal end of the main body of an exemplary menstrual receptacle applicator.

FIG. 4d is a schematic perspective view of the menstrual cup in the menstrual receptacle applicator of FIG. 4c with the push rod moved part of the distance towards the proximal end of the main body such that a portion of the menstrual cup is being ejected from the main body.

FIG. 4e is a schematic perspective view of the menstrual receptacle applicator of 4d with the push rod moved a full distance towards the proximal end of the main body such that the entire menstrual cup has been ejected from the main body.

FIG. 9 is a flow chart of a method of inserting a menstrual receptacle according to an exemplary embodiment.

Figure 1A:
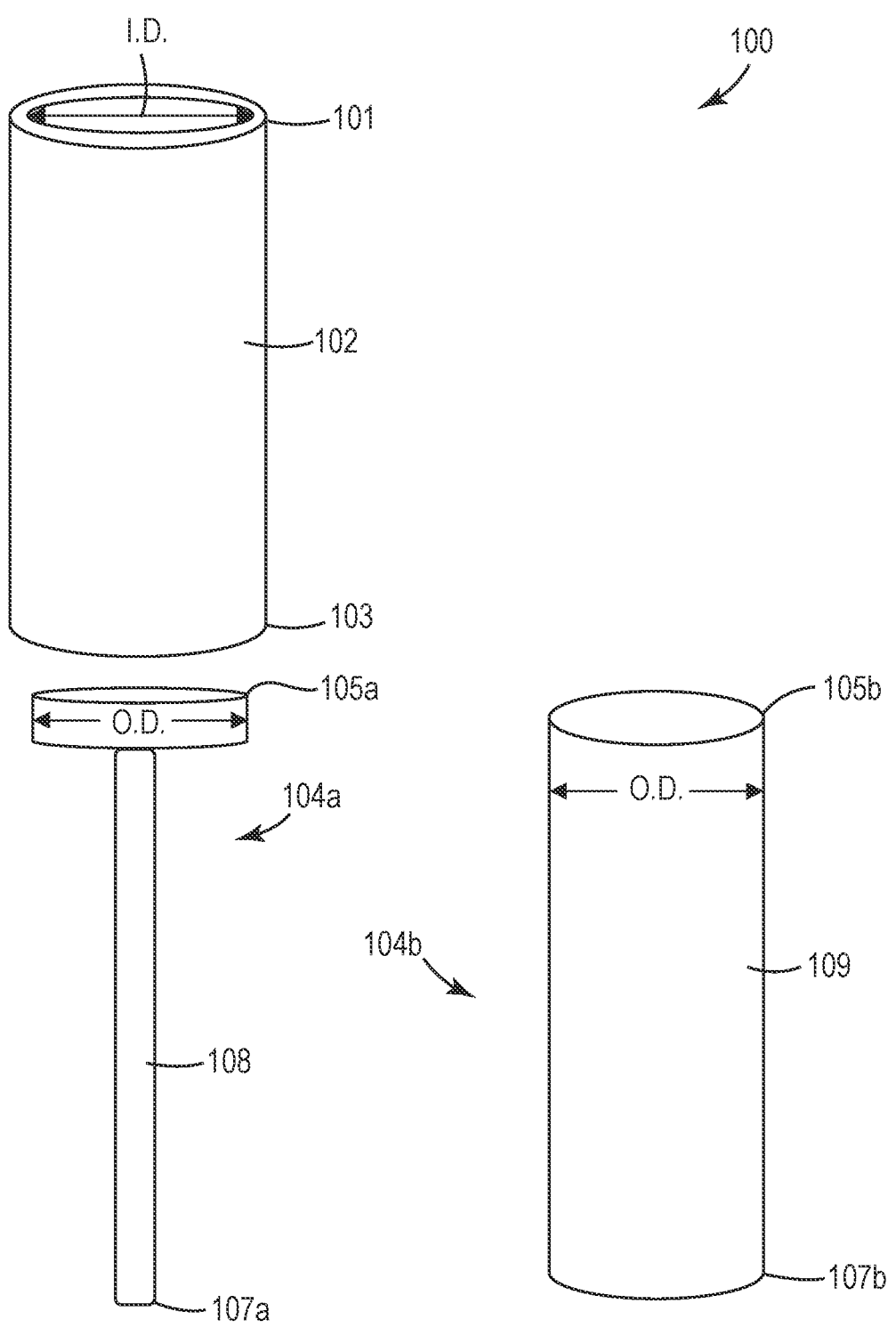
FIG. 1a is a schematic perspective view of an exemplary menstrual receptacle applicator, showing two options for a push rod, according to the present disclosure.

While the above-identified figures set forth various embodiments of the disclosure, other embodiments are also contemplated, as noted in the description. In all cases, this disclosure presents the invention by way of representation and not limitation. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

As used herein, "fluid" refers to the phase of matter that is intermediate between solid and gaseous, and encompasses fluids including solutions, dispersions, and emulsions, including menstrual secretions.

As used herein, "flange" refers to a protrusion from a portion of an end of a hollow body that extends at least partially into an opening defined by the end of the hollow body.

As used herein, "menstrual receptacle" refers to a menstrual product that is configured to collect and hold a volume of fluid within a continuous open area defined by at least one wall of the product. Menstrual cups and discs are common examples of menstrual receptacles. The continuous open area of menstrual receptacles is in contrast to absorbent menstrual products (e.g., pads, liners, tampons, etc.) that absorb and hold a volume of fluid in a discontinuous combination of absorbent materials (e.g., fibers, polymer particles, etc.) and interstitial space between the absorbent materials, as well as on exterior surface(s) of the absorbent product.

As used in this specification and the appended embodiments, the singular forms "a", "an", and "the" include plural referents unless the content clearly dictates otherwise. Thus, for example, reference to "a material" includes a mixture of two or more materials.

As used in this specification and the appended embodiments, the term "or" is generally employed in its sense including "and/or" unless the content clearly dictates otherwise. The term "and/or" means either or both. For example, the expression "A and/or B" means A, B, or a combination of A and B.

Unless otherwise indicated, all numbers expressing quantities, measurement of properties, and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The term "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, materials, or characteristics may be combined in any suitable manner in one or more embodiments.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

As mentioned above, menstrual receptacles have numerous advantages over other menstrual products, particularly over single-use absorbent products. However, it may be challenging for a user to learn a successful technique for inserting a menstrual receptacle, such as a menstrual cup or a menstrual disc. There may also be reluctance to perform the insertion by hand.

While several menstrual cup applicators have been developed to assist in inserting a menstrual cup, each has at least one disadvantage. For instance, patent document KR200486704Y1 (Song Young-hak) describes a menstrual cup insertion aid including a tubular main body sized to accommodate a folded menstrual cup. There are at least eight different ways to fold a menstrual cup for insertion, designed for the menstrual cup to pop fully open once inserted, to collect menstrual secretions within the cup. Such folds, however, still result in a cup having a relatively large size (e.g., effective diameter and/or flat width). For example, a menstrual cup having a diameter of 42 millimeters when open still typically has an effective largest diameter of 36 millimeters when folded into a C fold (see, e.g., FIGS. 6a-6b for a menstrual cup in a C fold). To accommodate a menstrual cup having a C fold, as disclosed in KR200486704Y1, the tubular main body of the menstrual cup insertion aid would have to have an inner diameter of greater than 30 millimeters, such as at least 31, 32, 33, 34, 35, or at least 36 millimeters. The larger the applicator diameter, the more likely a user is to experience discomfort at the time of insertion, such as due to stretching of the vaginal opening.

Patent document CN109833136A (Yin Zhentu) describes a menstrual cup applicator that includes a protective sleeve that receives a menstrual cup, and the sleeve is flexible for folding into a smaller shape for insertion. The size of the menstrual cup applicator is thus approximately the same as the size of the folded menstrual cup at the time of insertion. Patent application US 2019/0151136A1 (Garriga I Rodo) describes a menstrual cup applicator device that includes securing means, such as arms, to hold a folded menstrual cup in position for insertion. Likewise, the size is limited by the size of the folded menstrual cup at the time of insertion.

In contrast to such menstrual cup applicators, applicators configured for smaller menstrual products are known, such as tampon applicators. Tampon applicators, however, typically have a diameter range of 10 to 15 millimeters, which is too small for use with menstrual receptacles. Additionally, tampons have substantially different physical characteristics than menstrual receptacles, such as menstrual cups and menstrual discs, and thus requirements for tampon applicators are significantly different than requirements for menstrual receptacle applicators. First, tampons are composed of absorbent materials such as cotton and rayon fibers, which readily slide with minimal friction through applicators made of materials such as plastic and cardboard. Indeed, tampon applicators generally include a means for retaining the tampon within the applicator to prevent the tampon from sliding out prior to insertion, typically one or more flexible flanges that protrude from an end of the applicator body and extend at least partially into the opening to retain the tampon until the proper time of insertion, or a pinched end of the applicator body that subsequently expands enough to release the tampon during insertion upon pushing of a rod up through the applicator body. Second, the small amount of friction between the tampon and applicator body allows the use of materials for the applicator to be somewhat flexible, for instance push rods made of thin plastic or cardboard, because a low amount of force is required to urge the tampon through the applicator body at the time of insertion.

In contrast to the requirements for tampon applicators, menstrual receptacle applicators are larger than 15 millimeters to accommodate menstrual receptacles that are substantially larger than tampons, as well as including a more rigid push rod to successfully overcome the friction between the material of the menstrual receptacle (e.g., silicone polymer, latex rubber, etc.) and the main body of the applicator at the time of insertion without causing structural failure of the push rod (e.g., collapsing of the push rod). Further, the high friction between the material of the menstrual receptacle and the main body of the applicator generally allows greater design freedom for an opening of the main body as the menstrual receptacle typically does not have to be restrained from sliding or falling out of the main body during handling.

Figures 4A, 4B, 4C:
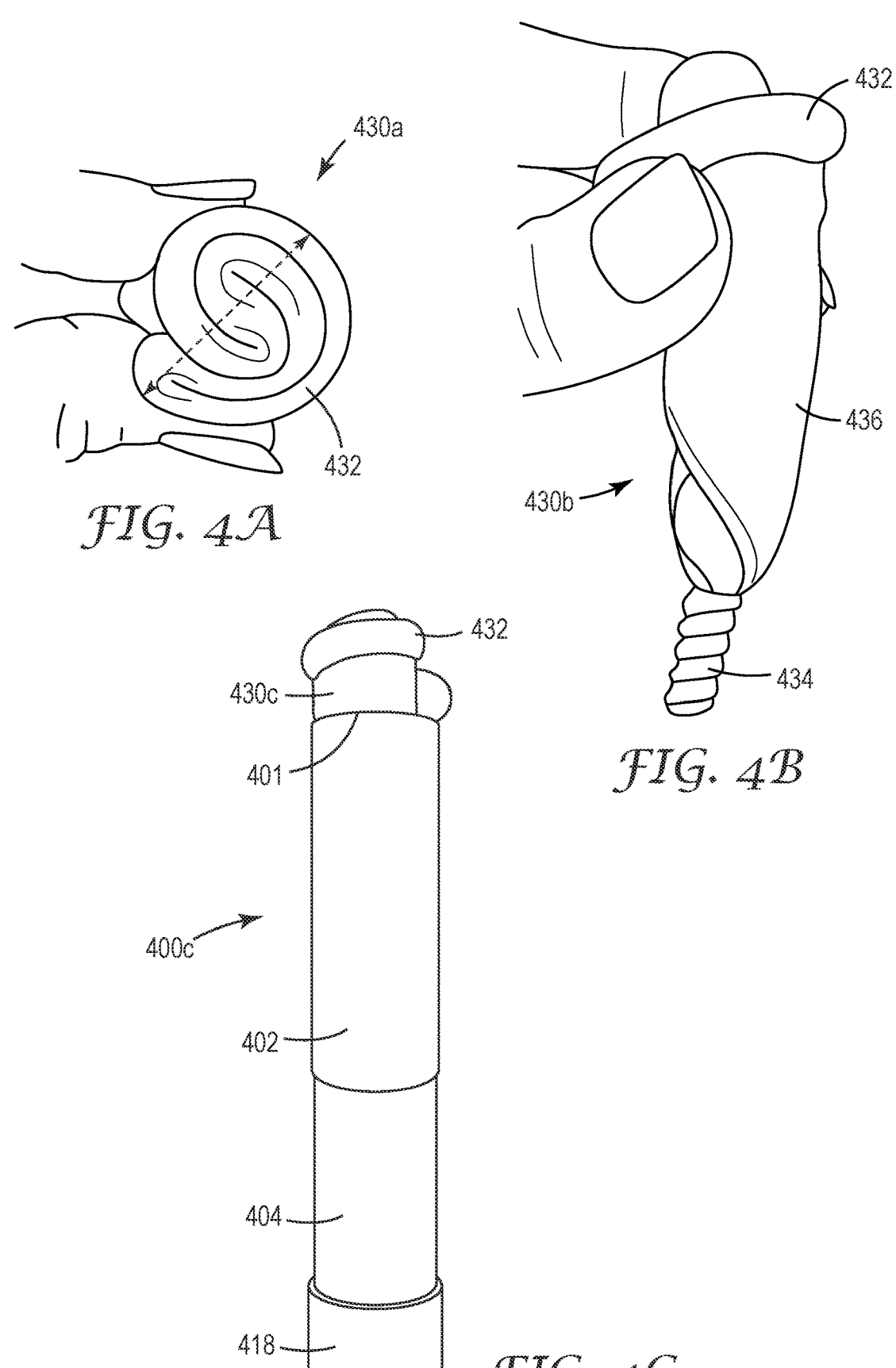
Figure 6A:
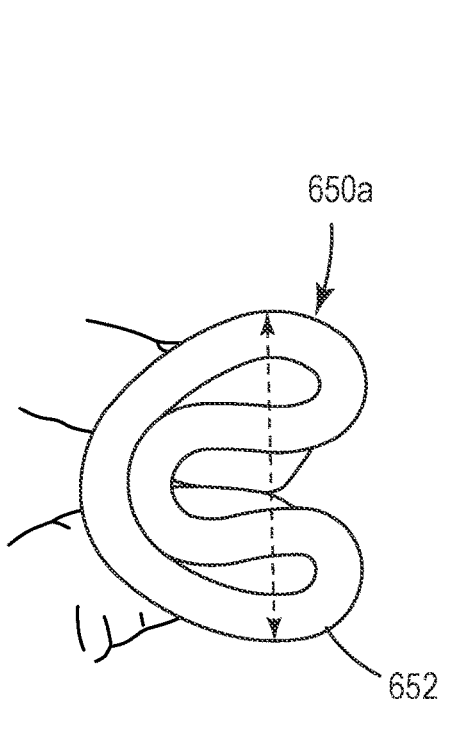
FIG. 6a is a schematic top view of a menstrual cup in a C fold.

It has been discovered that a menstrual cup can be rolled (e.g., into a spiral) to substantially decrease the largest effective diameter of the rolled cup as compared to a conventionally folded menstrual cup. Moreover, it has been discovered that the rolled menstrual cup still pops fully open once inserted for use such that a fold is not necessary for successful insertion. For instance, Table 1 below reports the difference in diameter across the top of each menstrual cup of four different sized cups, which is the largest location on each of the open, rolled, and C folded configurations. Referring to FIG. 4a, the double-ended arrow indicates the location a rolled menstrual cup was measured for diameter. Referring to FIG. 6a, the double-ended arrow indicates the location a menstrual cup having a C fold was measured for cup diameter. The diameters of the open cups are reported by the manufacturer and include the diameter across the top of a fully open menstrual cup (see, e.g., the menstrual cup 430e in FIG. 4e).

TABLE 1

| Diameter across the top of menstrual cups | | |
|---|---|---|
| Open Cup Diameter (mm) | Rolled Cup Diameter (mm) | C Folded Cup Diameter (mm) |
| 41 | 27 | 38 |
| 42 | 27 | 36 |
| 45 | 29 | 41 |
| 46 | 30 | 43 |

Rolling the cup decreased its effective diameter by an amount of about 9 to 13 millimeters (e.g., from 41-46 mm when open down to 27-30 mm when rolled), which is a significant difference and enables the use of a substantially smaller applicator. Moreover, use of a menstrual receptacle applicator according to at least certain embodiments of the present disclosure enables the use of a rolled cup because the applicator maintains the rolled configuration of the cup during the initial insertion process, keeping the effective diameter at the top of the cup smaller than that of the same cup in a folded configuration. In contrast, folding the cup into a C fold decreased its effective diameter by an amount of only about 3 to 6 millimeters (e.g., from 41-46 mm when open down to 38-43 mm when folded). It might be possible to place a lower portion of a cup having a C fold into an open proximal end of the main body of a menstrual receptacle applicator having an inner diameter of 16-30 mm at the proximal end. However, not only would less of the length of the folded cup fit into the main body than the same cup instead having a rolled configuration, but also the effective diameter at the top of the C folded cup would be significantly larger than the effective diameter of the same cup having a rolled configuration, which is undesirable for a user.

In a first aspect, a menstrual receptacle applicator is provided. The menstrual receptacle applicator comprises:

a) a hollow cylindrical main body defining an open proximal end and an open distal end, the main body having an inner diameter of 16 millimeters (mm) to 30 mm at the proximal end and configured to house at least a portion of a menstrual receptacle; and b) a push rod dimensioned to be inserted into and reciprocally moved within the main body.

The menstrual receptacle applicator may be formed of any suitable material, preferably a non-porous material, for instance and without limitation, plastic (preferably medical-grade plastic) (e.g., acrylonitrile butadiene styrene (ABS), polypropylene, polyethylene, silicone, polylactic acid, etc.), wood (e.g., bamboo), metal (e.g., steel, aluminum, etc.), or any combination thereof. Preferably, the applicator is formed of a material that can be washed and sanitized with minimal damage to the material such that the applicator may be reused in a sanitary manner. The applicator may be manufactured via injection molding, blow molding, woodworking, metal casting, or additive manufacturing, as known to those of skill in the art.

Referring to FIG. 1*a*, a schematic perspective view is provided of an exemplary menstrual receptacle applicator 100. The applicator 100 comprises a hollow cylindrical main body 102 defining an open proximal end 101 and an open distal end 103. Importantly, the main body 102 has an inner diameter (I.D., indicated in FIG. 1*a* by the double-ended arrow) of 16 millimeters (mm) to 30 mm at the proximal end 101 and is configured to house at least a portion of a menstrual receptacle (e.g., a menstrual cup, a menstrual disc, or a future developed menstrual receptacle). In certain embodiments, at the proximal end, the main body has an I.D. of 16 mm or greater, 17 mm, 18 mm, 19 mm, 20 mm, 21 mm, 22 mm, 23 mm or 24 mm or greater; and 30 mm or less, 29 mm, 28 mm, 27 mm, 26 mm, 25 mm, 24 mm, 23 mm, or 22 mm or less. In select embodiments, at the proximal end, the main body has an I.D. of 18 mm to 28 mm, 18 mm to 26 mm, or 18 mm to 24 mm.

The menstrual receptacle applicator 100 further comprises a push rod dimensioned to be inserted into and reciprocally moved within the main body. Two different embodiments of suitable push rods, 104*a* and 104*b*, are illustrated in FIG. 1*a*. The push rod 104*a* comprises a cylindrical head 105*a* at a proximal end of the push rod 104*a*, the cylindrical head 105*a* having an outer diameter (O.D.) configured to fit within the inner diameter of the main body 102. The push rod 104*a* further comprises a handle 108 for a user to grip the push rod 104*a* and urge the push rod 104*a* (e.g., reciprocally) into and out of the main body 102 as needed. The handle 108 includes a distal end 107*a* located opposite the length of the push rod 104*a* from the cylindrical head 105*a*. The push rod 104*b* comprises a solid cylindrical body 109 having an outer diameter (O.D.) configured to fit within the inner diameter of the main body 102, a proximal end 105*b*, and a distal end 107*b* located opposite the length of the push rod 104*b* from the proximal end 105*b*. In any embodiment, in use, the proximal end of the push rod is inserted into the distal end of the main body.

Figure 1B:
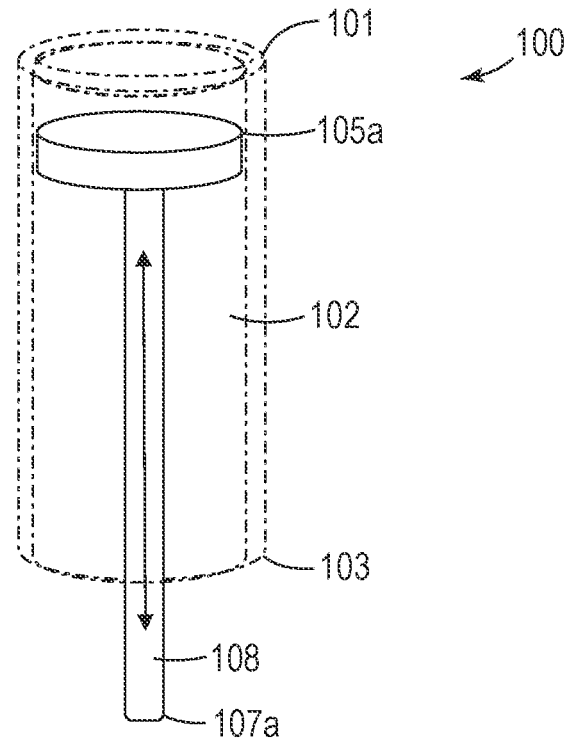
FIG. 1b is a schematic perspective view of the exemplary menstrual receptacle applicator of FIG. 1a in which a push rod is inserted into the main body.

FIG. 1B provides a schematic perspective view of the push rod 104*a* engaged with the main body 102. The double-ended arrow indicates the directions in which the push rod 104*a* may be reciprocally moved within the main body 102. In some cases, the outer diameter of the proximal end (e.g., cylindrical head 105*a*) of a push rod is configured to be sufficiently smaller than the inner diameter of the main body to readily be moved within the main body, but sufficiently large to minimize movement at an angle within the main body other than generally straight in and out. In any embodiment of a menstrual receptacle applicator of the present disclosure, the push rod optionally comprises a ledge at the proximal end. In some cases, the ledge is provided by a cylindrical head such as cylindrical head 105*a* that supplies a continuous support for a menstrual receptacle when the push rod is in contact with the menstrual receptacle. Another option for the ledge is a protrusion that extends inwardly into an open proximal end from the proximal end of a hollow cylindrical push rod, to provide a larger area of support for the menstrual receptacle than the same push rod lacking the protrusion. When present, the ledge typically protrudes around the entire circumference of a push rod having a hollow cylindrical shape.

Referring to FIGS. 2*a*-2*f*, in any menstrual receptacle applicator of the present disclosure, a friction fit may be provided between a portion of the push rod and a portion of the main body. The purpose of a friction fit (or an interference fit) is to minimize the likelihood of the main body and the push rod from inadvertently separating from each other (e.g., the push rod falling out of the main body due to gravity) while a user is manipulating one or both of the main body or push rod during use of the menstrual receptacle applicator. Such a friction fit may be achieved using at least one protrusion disposed on an exterior surface of the push rod, at least one protrusion disposed on an interior surface of the main body, a clasp formed between a portion of the main body and the push rod, a compression fit between the main body and the push rod, or any combination thereof. When a protrusion is employed, it may be integrally formed with the surface of the main body or the push rod, or may be a separate material (e.g., a piece of rubber disposed on the interior surface of the main body and/or a piece of rubber disposed on the exterior surface of the push rod).

Figure 2A:
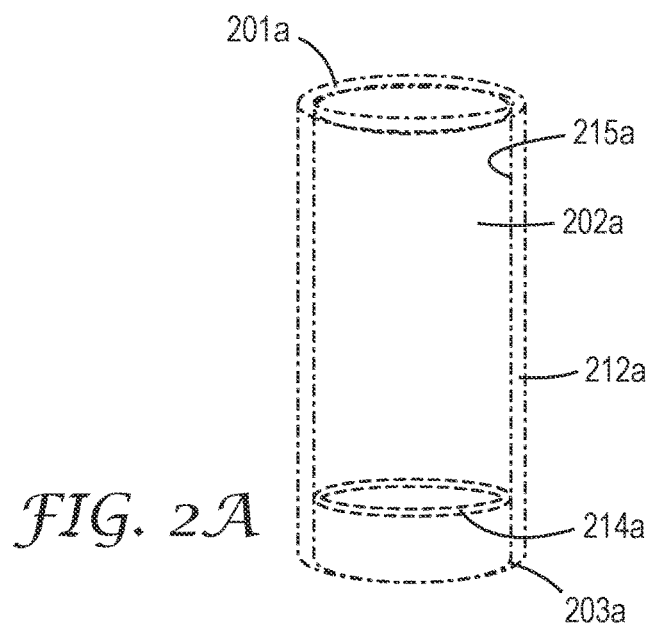
FIG. 2a is a schematic perspective view of a main body of a menstrual receptacle applicator having a protrusion disposed on an interior surface, according to the present disclosure.

FIG. 2*a* illustrates a main body 202*a* that comprises a protrusion 214*a* located on an interior surface 215*a* of the main body 202*a* that extends into the opening of the hollow cylindrical main body to provide a friction fit with a push rod (not shown). In this case, the protrusion 214*a* is disposed closer to the distal end 203*a* than the proximal end 201*a* of the main body 202*a*. An advantage of locating the structure that provides friction fit closer to the distal end of the main body (and/or closer to the proximal end of the push rod) includes enabling a greater range of free reciprocal motion of the push rod within the main body. However, in some embodiments, it may instead be preferable to locate the structure that provides the friction fit closer to the proximal end of the main body (and/or closer to the distal end of the push rod) to provide a more compact (e.g., shorter) applicator when the main body and the push rod are engaged. Accordingly, a structure that provides the (optional) friction fit may be located anywhere along the length of the main body and/or the push rod for any menstrual receptacle applicator according to the present disclosure.

Figure 2B:
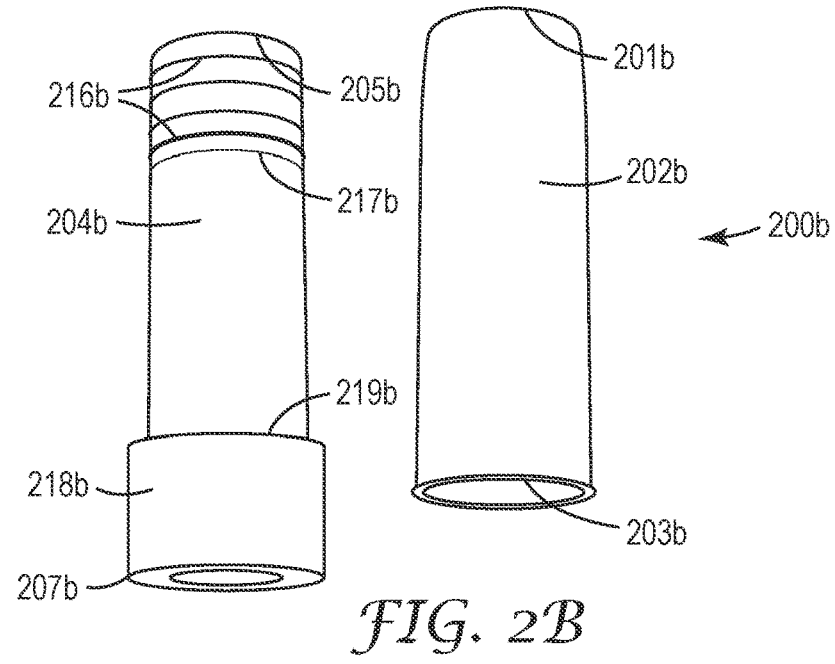
FIG. 2b is a schematic perspective view of an exemplary menstrual receptacle applicator including a push rod having a plurality of protrusions disposed on an exterior surface.

FIG. 2*b* illustrates an exemplary menstrual receptacle applicator 200*b* comprising a main body 202*b* and a push rod 204*b*, each having a shape that is generally a hollow cylinder. The push rod 204*b* includes a plurality (e.g., 4) protrusions 216*b* each extending circumferentially around an exterior surface 217*b* of the push rod 204*b* and longitudinally spaced apart from each other along the length of the main body 204*b*. The protrusions 216*b* are located closer to the proximal end 205*b* of the push rod 204*b* than the distal end 207*b*. Further, a grip 218*b* is formed at the distal end 207*b* of the push rod 204*b*. The grip 218*b* comprises material that extends circumferentially around a portion of the exterior surface 217*b* of the push rod 204*b*, either the same material that the push rod 204*b* is formed of (e.g., the grip 218*b* may be integrally formed as a part of the push rod 204*b*, as in this embodiment) or could be a separate material attached the push rod 204*b* towards the distal end 207*b* (e.g., an elastomeric polymer). Often, a ledge 219b that extends outwardly from the exterior surface 217b of the push rod 204b is present, having a width that is the difference between an outer diameter of the grip 218b and the exterior surface 217b adjacent to the grip 218b. A grip may be useful in any embodiment of a push rod and/or a main body of an exemplary menstrual receptacle applicator according to the present disclosure, for instance to provide a convenient handle for a user and/or to provide a more rigid push rod.

The main body 202b of this applicator 200b has an outer diameter of the distal end 203b of the main body 202b that is larger than an outer diameter of the proximal end 201b of the main body 202b. Additionally, the distal end 203b of the main body 202b of this applicator 200b is formed to flare outwards and have a shape of a small lip. In this embodiment, the difference in outer diameter is provided by a slight reduction in the size of the full circumference of the proximal end 201b of the main body 202b. Such a reduction in the size of the full circumference of the proximal end of a main body is in significant contrast to a flange, which is defined as a protrusion from a portion of an end of a hollow body that extends at least partially into an opening defined by the end of the hollow body. In particular, it is the difference between a portion of an end of the hollow body and the entire circumference of an end of the hollow body. One or more flanges are included in certain tampon applicators, usually configured to prevent a tampon from falling out of the applicator prior to insertion, and any flanges present are sufficiently flexible to bend outwardly to allow passage of the tampon out of the applicator during insertion. In certain embodiments of a menstrual receptacle applicator according to the present disclosure, the proximal end of the main body is free of any flanges formed thereon. Not only are one or more flanges typically unnecessary to prevent a menstrual receptacle from falling out of the main body, but also the force required to overcome the friction between the menstrual receptacle and the main body of the applicators described herein may be large enough to break the flange(s) as the menstrual receptacle is inserted into the vaginal opening of a user, which would be highly undesirable and risk injury to the user.

Further to the requirement, as compared to a tampon applicator, of a more rigid push rod to successfully overcome the friction between the material of the menstrual receptacle and the main body of the applicator at the time of insertion without causing structural failure of the push rod, in some embodiments of the menstrual receptacle applicator, the main body is formed of a cylindrical wall (e.g., has a hollow cylindrical shape), the push rod is hollow and formed of a cylindrical wall (e.g., has a hollow cylindrical shape), and the cylindrical wall of at least a portion of the push rod is thicker than the cylindrical wall of the main body. For example, such an applicator is shown in FIG. 2b, wherein at the distal end 207b, a thickness of the push rod 204b can be seen to be thicker than the distal end 203b of the main body 202b. Including a thicker wall will increase the rigidity of the push rod, which may be needed depending on what material is used to form the push rod. In certain embodiments, (e.g., at least a portion) of a cylindrical wall of the push rod has a thickness of 1 mm or greater, 2, 3, 4, or 5 mm or greater; and 10 mm or less, 9 mm, 8 mm, 7 mm, 6 mm, or 5 mm or less.

Figure 2C:
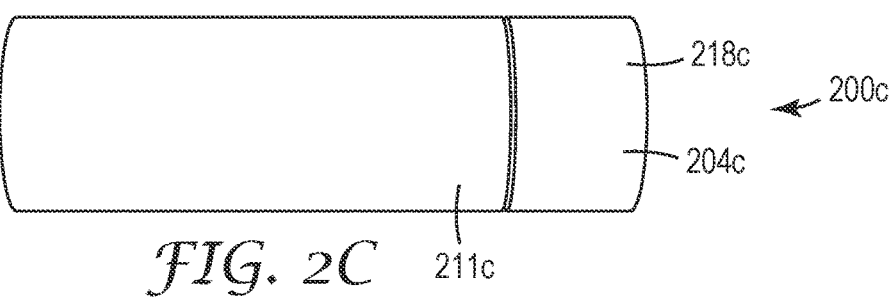
FIG. 2c is a schematic perspective view of the exemplary menstrual receptacle applicator of FIG. 2b assembled and including a cap disposed over the main body.

FIG. 2c illustrates an exemplary menstrual receptacle applicator 200c (e.g., the menstrual receptacle applicator 200b of FIG. 2b) comprising a main body (not visible), a push rod 204c fully inserted into the main body, and further comprising a cap 211c disposed over the main body and directly adjacent to the grip 218c of the push rod 204c. A cap is optionally included with any exemplary menstrual receptacle applicator according to the present disclosure, the cap being dimensioned to receive the main body and engage with the push rod (e.g., with a distal end, an exterior surface, or a grip, if present) when the push rod is fully inserted into the main body. An advantage of including a cap is that the main body and most of the push rod can be protected from contamination by debris, microorganisms, etc., when the menstrual receptacle applicator is not in use. Further, the cap can provide a discreet cover shielding the applicator from others' view.

FIG. 2d illustrates an exemplary menstrual receptacle applicator 200d comprising a main body 202d and a push rod 204d, each having a shape that is generally a hollow cylinder. The main body 202d and the push rod 204d are each dimensioned to provide a compression fit when the push rod 204d is inserted into the main body 202d. In this embodiment, a friction fit is provided between the main body 202d and the push rod 204d by sizing the opening at the distal end 203d of the main body 202d to be slightly smaller than the inner diameter along most of the length of the main body 202d. The push rod 204d is sized such that when the push rod 204d is inserted into the distal end 203d of the main body, there is a resistance at the distal end 203d that is overcome by flexibility of the main body outwards to accommodate the push rod 204d. Such compression fits are known to those of skill in the art. This push rod 204d further comprises a grip 218d located at a distal end of the push rod 204d opposite the length of the push rod 204d from the proximal end 205d.

Additionally, each of the main body 202d and the push rod 204d of this embodiment is shaped to have a reduction in the size of the full circumference of the proximal end 201d of the main body 202d and of the proximal end 205d of the push rod 204d, respectively, resulting in a smaller inner diameter at the proximal end than the distal end of each. Designing the proximal ends of the parts of any menstrual receptacle applicator of the present disclosure to be the smallest diameter portion of the main body and push rod may be advantageous in being more comfortable for a user at the time of insertion, especially if the reduction in diameter from the length of the parts to the proximal ends provides a curved or rounded shape. The main body 202d of this applicator 200d further comprises a ledge 213d that extends circumferentially around an exterior surface 217d of the main body 202d at the distal end 203d of the main body 202d. The ledge 213d can advantageously provide a convenient location for a user to hold the main body 202d when the applicator 200d is in use. Thus, a ledge may be provided on an exterior surface of the main body (usually at or near the distal end) of any menstrual receptacle applicator of the present disclosure.

FIG. 2e illustrates an exemplary menstrual receptacle applicator 200e comprising a main body 202e and a push rod 204e, each having a shape that is generally a hollow cylinder and comprising a portion of a clasp to engage when the push rod 204e is partially inserted into the main body 202e. More particularly, the main body 202e comprises a first portion of a clasp 221e disposed at the distal end 203e of the main body 202e. The push rod 204e comprises a second portion of a clasp 223e disposed approximately halfway between the proximal end 205e and the distal end 207e of the push rod 204e. In any embodiment, the first and second portions of an optional clasp can be integrally formed with an exterior surface of the main body and the push rod, respectively, or can be separate parts attached to the main body and the push rod. The clasp structure is not particularly limited; any clasp may be suitable (e.g., including clasps used in cosmetic containers like compacts), such as including two flexible portions that overlap to engage the clasp.

FIG. 2*f* illustrates the exemplary menstrual receptacle applicator of FIG. 2*e* assembled, with the two portions (221*f*, 223*f*) of the clasp engaged with each other, which provides a friction fit between the main body 202*f* and the push rod 204*f*. When the clasp is in a closed position (i.e., the first portion of the clasp 221*f* is engaged with the second portion of the clasp 223*f*), the push rod 204*f* is secured from sliding out of the main body 202*f* due to gravity. At the time that a user wants to fully insert the push rod 204*f* into the main body 202*f*, the user can disengage the first 221*f* and second 223*f* portions of the clasp and typically rotates at least one of the push rod 204*f* or the main body 202*f* with respect to the other such that the first 221*f* and second 223*f* portions of the clasp are separated from each other laterally around the main body 202*f* and push rod 204*f* to prevent the first 221*f* and second 223*f* portions of the clasp from contacting each other as the push rod 204*f* is more fully inserted into the main body 202*f*.

Figures 3A, 3B:
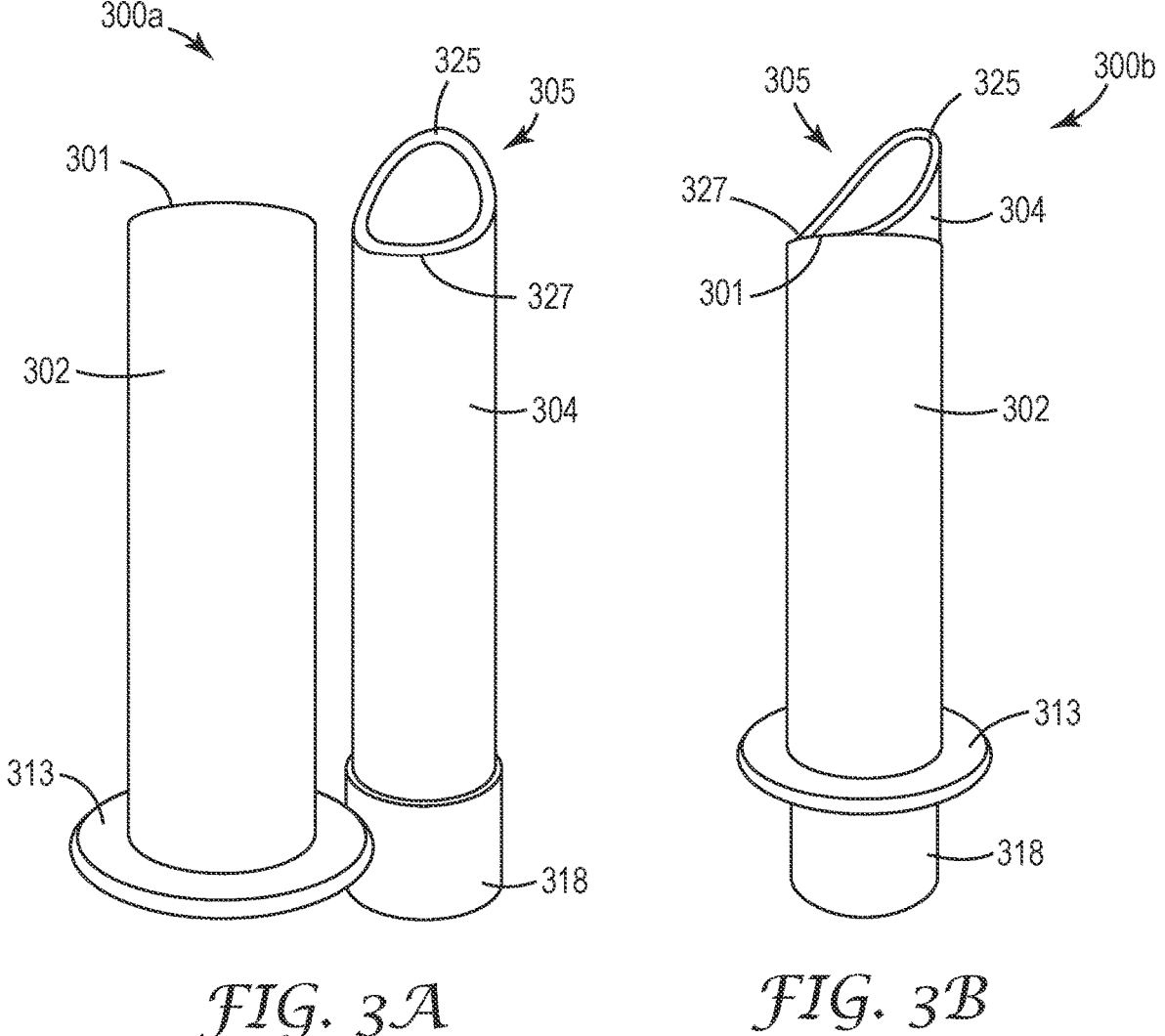
FIG. 3a is a schematic perspective view of an exemplary menstrual receptacle applicator including a main body and a push rod with a tapered shape at its proximal end.
FIG. 3b is a schematic perspective view of the exemplary menstrual receptacle applicator of FIG. 3a assembled.

Referring to FIG. 3*a*, a schematic perspective view of an exemplary menstrual receptacle applicator 300*a* is provided. The applicator 300*a* comprises a main body 302 and a push rod 304, each having a shape that is generally a hollow cylinder. The push rod 304 comprises a tapered shape 325 at the proximal end 305 of the push rod 304. As used herein, "tapered" refers to a portion of the push rod material at the proximal end coming to a (e.g., rounded) point, wherein a length between the distal end and the proximal end of a portion of the push rod that ends in the point is greater than a length between the distal end and the proximal end of the remaining portion of the push rod. Advantageously, providing a tapered shape may assist in ensuring that the menstrual receptacle fully opens during the insertion process. For instance, often a user is advised to run a finger along the top edge of the inserted menstrual cup to ensure it is opened and has formed a tight seal with the vaginal walls; rotating the tapered shape of the push rod may advantageously serve the same purpose. In this embodiment, the main body 302 includes a ledge 313 opposite the length of the main body from the proximal end 301 and the push rod 304 includes a grip 318 at the (distal) end opposite the tapered shape 325. FIG. 3*b* illustrates the exemplary menstrual receptacle applicator of FIG. 3*a* assembled, including the push rod 304 being fully inserted into the main body 302. The tapered shape 325 is visible extending beyond the proximal end 301 of the main body 302, with its lowest point 327 nearly even with the proximal end 301 of the main body 302.

Referring to FIGS. 4*a*-4*e*, aspects of a use of an exemplary menstrual receptacle applicator 400*c*-400*e* are described. FIG. 4*a* provides a schematic top view of a rolled menstrual cup 430*a* and FIG. 4*b* is a schematic side view of a rolled menstrual cup 430*b* (e.g., two views of the same rolled menstrual cup) to be used in a menstrual receptacle applicator according to the present disclosure. As mentioned above, it has been discovered that a menstrual cup can be rolled (e.g., into a spiral, as shown in FIGS. 4*a*-4*b*) to substantially decrease the largest effective diameter of the rolled cup as compared to a conventionally folded menstrual cup, plus that the rolled menstrual cup still pops fully open once inserted such that it is not necessary to use a folded configuration for successful insertion and use. The double-ended arrow across the top 432 of the menstrual cup 430*a* in FIG. 4*a* indicates where the diameter of the rolled menstrual cup 430*a* gets measured. As apparent from the side view of the rolled menstrual cup 430*b* in FIG. 4*b*, the top 432 is the largest portion of the rolled menstrual cup 430*b*, whereas the body 436 and the end (located distal to the top 432) have smaller effective diameters. Often, the end of a menstrual cup will have a stem disposed at the closed end (as does the end 434 in FIG. 4*b*) for grasping by a user to assist in removal of the menstrual cup following use.

FIG. 4*c* provides an illustration of how the rolled menstrual cup 430*c* (e.g., rolled as shown in FIGS. 4*a*-4*b*) can be suitably disposed partially into the proximal end 401 of the main body 402 of an exemplary menstrual receptacle applicator 400*c*. Accordingly, the proximal end 401 of the main body 402 is configured to house at least a portion of a rolled menstrual cup 430*c*. Due to the size of the rolled menstrual cup 430*c* and the generally high level of friction of the cup material with the main body 402, the rolled menstrual cup 430*c* is usually introduced into the main body 402 through the opening at the proximal end 401. Having the top 432 of the rolled menstrual cup 430*c* protruding from the proximal end 401 of the main body 402 allows for a main body 402 having a smaller inner diameter to be used than if the entire rolled menstrual cup 430*c* was disposed within the main body 402. For example, a large menstrual cup having a diameter measured at the top when rolled of about 35 mm can typically still be used with a menstrual receptacle applicator having an inner diameter of just 30 mm. It is generally expected that the smaller the diameter of the main body of a menstrual receptacle applicator, the greater the comfort for the user of the applicator during insertion. In the embodiment of FIG. 4*c*, the assembled menstrual receptacle applicator 400*c* is illustrated, with the push rod 404 partially inserted into the main body 402. Each of the main body 402 and the push rod 404 has a shape that is generally a hollow cylinder. The push rod 404 further comprises a grip 418 to assist in a user grasping the push rod 404.

With the rolled menstrual cup 430*c* positioned partially within the main body 402 of the assembled menstrual receptacle applicator 400*c*, for instance as shown in FIG. 4*c*, the applicator 400*c* is ready for use to insert the menstrual cup 430*c* into a vaginal opening of a user. To implement insertion, the user (e.g., reciprocally) applies force to the push rod 404 (e.g., using an optional grip 418) to urge the push rod 404 further up through the hollow interior opening of the main body 402. FIG. 4*d* provides an illustration of a point in time when the push rod 404 has been moved part of the way closer to the proximal end 401 of the main body 402. As can be seen in FIG. 4*d*, the menstrual cup 430*d* has been partially ejected from the proximal end 401 of the main body 402 such that a portion of the body 436 of the menstrual cup 430*d* is visible and the top 432 is already starting to open. Also, the push rod 404 has been moved part of the distance towards the proximal end 401 of the main body 402, for instance as compared to the position of the push rod 404 in FIG. 4*c*. FIG. 4*e* provides an illustration of a point in time when the push rod 404 has been moved by the user the full distance towards the proximal end 401 of the main body 402, such that the entire menstrual cup 430*e* has been ejected from the main body 402 of the menstrual receptacle applicator 400*e*. As shown in FIG. 4*e*, the menstrual cup 430*e* is fully opened, after having been rolled at the time of placing the cup into the main body 402.

In any embodiment of the menstrual receptacle applicators according to the present disclosure, the receptacle is optionally a menstrual cup having a maximum (e.g., measured at the top end) outer diameter when not rolled (i.e., open, such as shown in FIG. 4*e*) of 35 mm or greater, 36 mm, 37 mm, 38 mm, 39 mm, 40 mm, 41 mm, 42 mm, 43 mm, 44 mm, 45 mm, or 46 mm or greater; and 55 mm or less, 54 mm, 53 mm, 52 mm, 51 mm, 50 mm, 49 mm, 48 mm, 47 mm, or 46 mm or less; e.g., 35 mm to 55 mm. In select embodiments, the receptacle is a menstrual cup having a maximum outer diameter when not rolled of 40 mm to 48 mm.

Figure 5A:
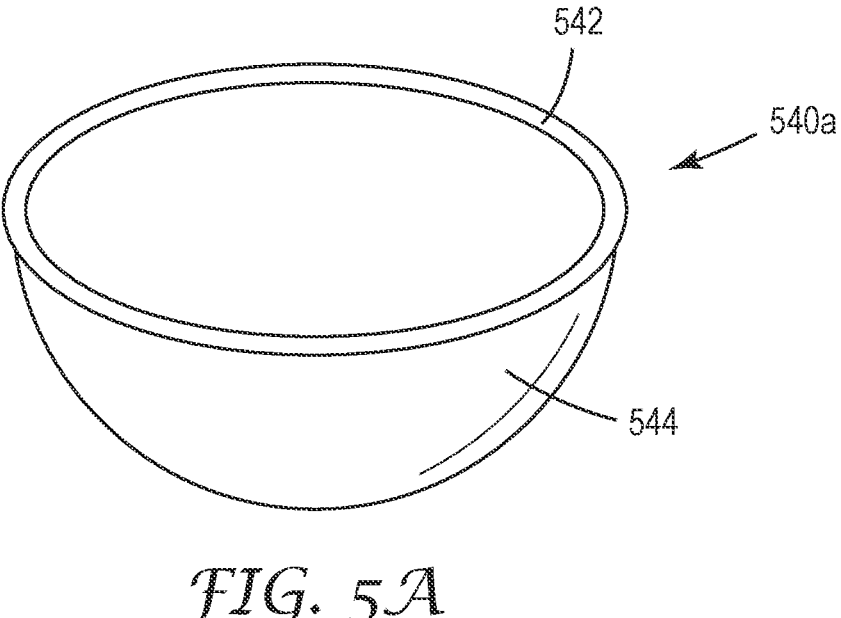
FIG. 5a is a schematic perspective view of a menstrual disc to be used in a menstrual receptacle applicator according to the present disclosure.
Figure 5B:
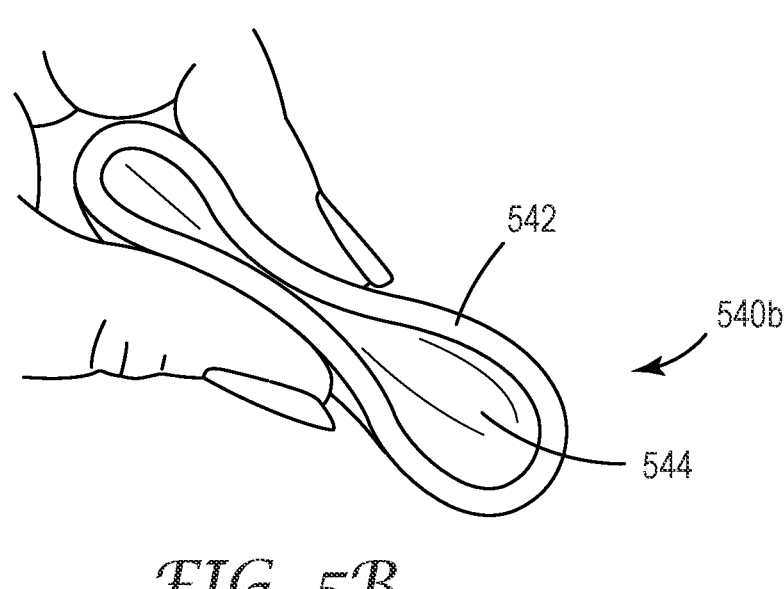
FIG. 5b is a schematic perspective view of a compacted menstrual disc to be used in a menstrual receptacle applicator according to the present disclosure.
Figure 5C:
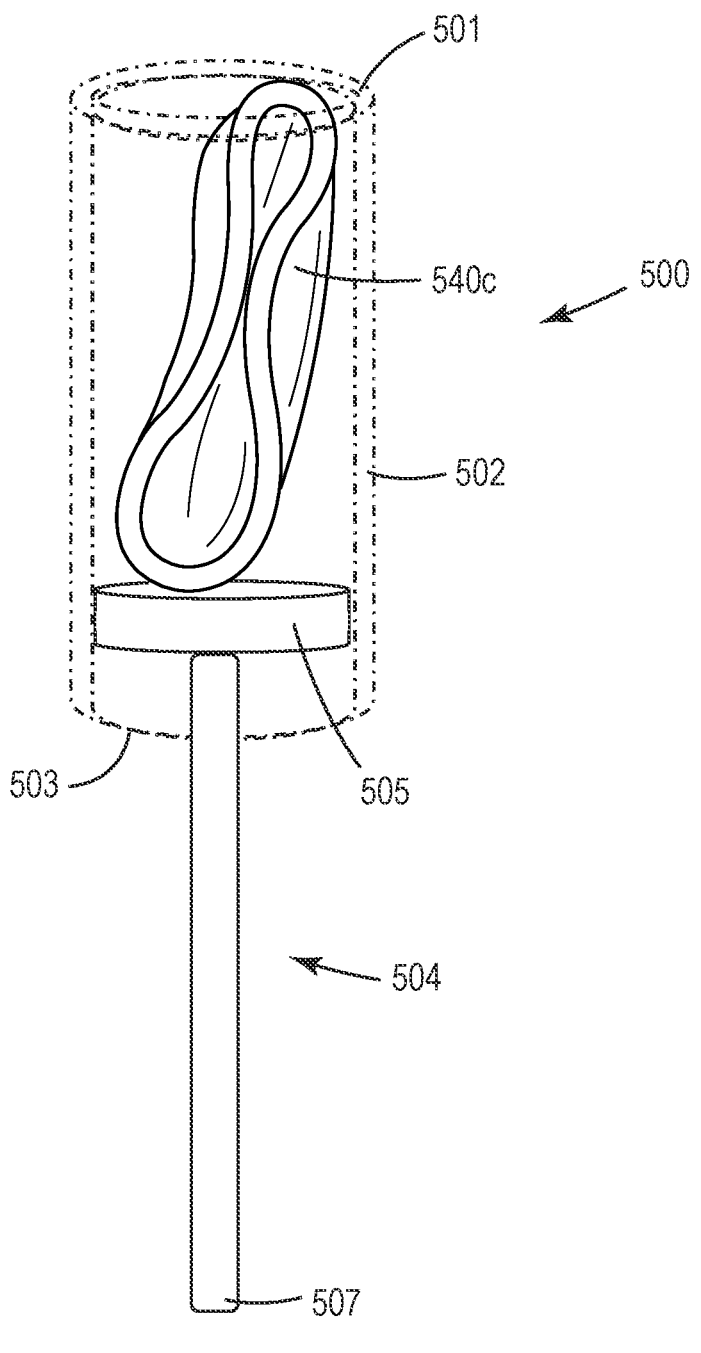
FIG. 5c is a schematic perspective view of a compacted menstrual disc disposed in the main body of an exemplary menstrual receptacle applicator.

Advantageously, the menstrual receptacle applicators according to the present disclosure are not limited to use solely with menstrual cups, making the applicators described herein more versatile than prior menstrual product applicators. Another suitable menstrual receptacle is a menstrual disc. Generally, a menstrual disc is wider (e.g., two to three inches in diameter) and shallower than a menstrual cup, as a disc is designed to be placed in a wider area adjacent to the cervix while a cup is designed to be placed in a narrower vaginal canal. Referring to FIG. 5a, an illustration is provided of a menstrual disc 540a having a top edge 542 and a body 544. Similar to menstrual cups, the top edge of a menstrual disc is typically configured to be resilient and keep the disc fully open. Referring to FIG. 5b, an illustration is provided of a compacted menstrual disc 540b pinched (e.g., flattened) between a user's fingers. FIG. 5c is a schematic perspective view of a compacted menstrual disc 540c disposed within the hollow cylindrical main body 502 of an exemplary menstrual receptacle applicator 500. The compacted menstrual disc 540c is usually placed in the proximal end 501 of the main body 502 but could alternatively be placed in the distal end 503 of the main body 502 prior to engaging the push rod 504 with the distal end 503 of the main body 502. Accordingly, the proximal end 501 of the main body 502 is configured to house at least a portion of a compacted menstrual disc 540c (e.g., either partially or fully disposed in the main body). In use, the head 505 of the push rod 504 would urge the compacted menstrual disc 540c up out of the main body 502 as a user moves the push rod 504 further towards the proximal end 501 of the hollow main body 502. It may be desirable to begin with the proximal end 501 of the main body inserted further into a vaginal canal (as opposed to just within the vaginal opening) of a user to assist in ejecting the menstrual disc 540c closer to the user's cervix.

Figure 6B:
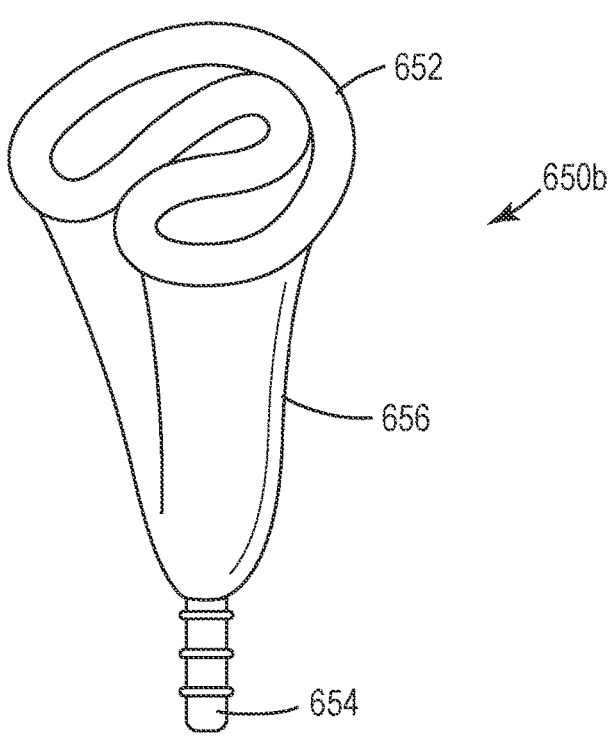
FIG. 6b is a schematic perspective view of a menstrual cup in a C fold.
Figure 7:
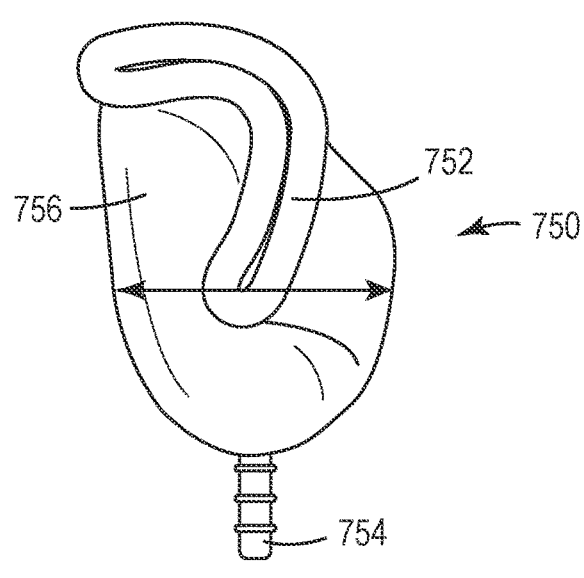
FIG. 7 is a schematic perspective view of a menstrual cup in a 7 fold.

In contrast to a compacted menstrual disc or a rolled menstrual cup, known folds for menstrual cups result in a smaller decrease in the effective diameter of the menstrual cup. Referring to FIGS. 6a-6b, illustrations are provided of a menstrual cup folded into a C fold. FIG. 6a is a top view of the folded menstrual cup 650a, with the double-ended arrow indicating the location across the top 652 that a menstrual cup having a C fold would be measured for cup diameter for insertion. FIG. 6b is a perspective view of a C folded menstrual cup 650b having a top 652, an end 654 (in the shape of a stem) and a body 656 between the top 652 and the end 654. Comparing FIGS. 4b and 6b it is apparent that the C fold does not compress the menstrual cup as much as rolling the cup into a spiral. Referring to FIG. 7, a menstrual cup 750 folded into a common 7 fold is illustrated. FIG. 7 is a perspective view of a 7 folded menstrual cup 750 having a top 752, an end 754 (in the shape of a stem) and a body 756 between the top 752 and the end 754. The double-ended arrow indicates the location across the body 756 that a menstrual cup having a 7 fold would be measured for effective cup diameter for at least partial insertion into a menstrual receptacle applicator. Comparing FIGS. 4b and 7 it is apparent that the 7 fold has little impact on decreasing the effective diameter of the menstrual cup, in contrast to rolling a menstrual cup into a spiral.

In a second aspect, a kit is provided. The kit comprises:

a) one or more menstrual receptacles; and
b) the menstrual receptacle applicator according to any embodiment of the first aspect described in detail above.

In certain embodiments, the at least one menstrual receptacle comprises a menstrual cup, e.g., a menstrual cup having a diameter as described in detail above. In certain embodiments, the one or more menstrual receptacles comprises a menstrual disc. The kit optionally further comprises a cap dimensioned to receive the main body and engage with the push rod when the push rod is fully inserted into the main body. The optional cap is as described in detail above with respect to the first aspect.

Figure 8:
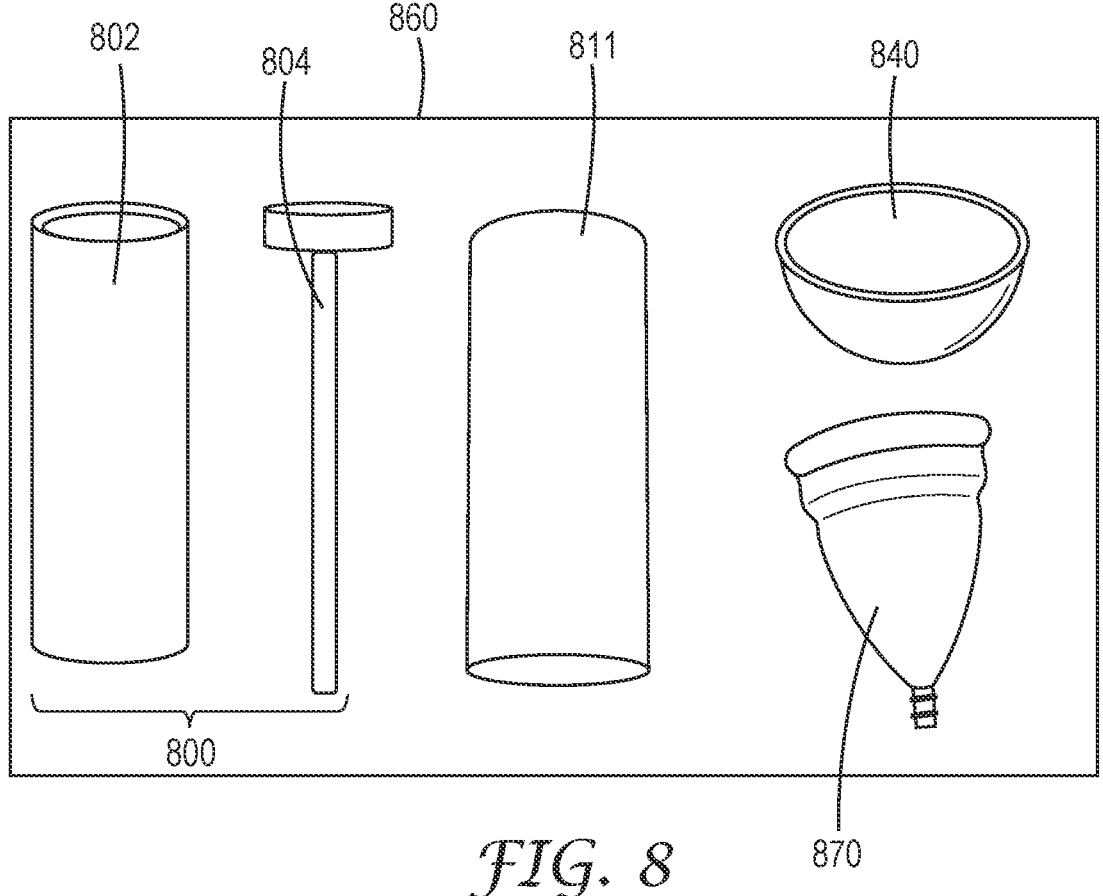
FIG. 8 is a schematic perspective view of a kit including an exemplary menstrual applicator, a cap, a menstrual cup, and a menstrual disc.

Referring to FIG. 8, an illustration is provided of a kit 860 comprising an exemplary menstrual applicator 800 comprising a main body 802 and a push rod 804. The kit 860 further comprises an optional cap 811 and two menstrual receptacles: a menstrual cup 870 and a menstrual disc 840. Only one menstrual receptacle is required; however, a user may want to have the option of selecting between different types of menstrual receptacles.

In a third aspect, a method is provided. The method comprises:

a) obtaining a menstrual receptacle applicator comprising:
  i) a hollow cylindrical main body defining an open proximal end and an open distal end, the main body having an inner diameter of 16 mm to 30 mm at the proximal end; and
  ii) a push rod dimensioned to be inserted into and reciprocally moved within the main body;
b) either 1) rolling a menstrual receptacle into a spiral to form a rolled menstrual receptacle or 2) flattening a receptacle to form a compacted menstrual receptacle;
c) at least partially inserting the rolled menstrual receptacle or the compacted menstrual receptacle into the proximal end of the main body;
d) inserting a proximal end of the push rod into the distal end of the main body;
e) inserting the proximal end of the main body containing the rolled menstrual receptacle or the compacted menstrual receptacle into a vaginal opening; and
f) pushing the push rod toward the proximal end of the main body until the proximal end of the push rod pushes the rolled menstrual receptacle or the compacted menstrual receptacle into the vaginal opening.

Usually, the method further comprises (e.g., step g)) removing the main body from the vaginal opening after step f).

The order of certain of the steps may be interchanged. For instance, in some embodiments step d) is performed before step c), such that the proximal end of the push rod is inserted into the distal end of the main body prior to the menstrual receptacle being inserted into the proximal end of the main body. In certain embodiments, step e) is performed before step d) such that the proximal end of the main body containing the menstrual receptacle is inserted into the vaginal opening prior to the proximal end of the push rod being inserted into the distal end of the main body.

In certain embodiments, the menstrual receptacle is a menstrual cup, e.g., a menstrual cup having a diameter as described in detail above. In certain embodiments, the menstrual receptacle is a menstrual disc. Often, the rolled menstrual receptacle or the compacted menstrual disc is partially inserted into the proximal end of the main body and a portion of the menstrual cup or the menstrual disc protrudes from the proximal end of the main body.

Referring to FIG. 9, a flow chart is provided. FIG. 9 comprises Step 910 to a) obtain a menstrual receptacle applicator comprising: i) a hollow cylindrical main body defining an open proximal end and an open distal end, the main body having an inner diameter of 16 millimeters (mm) to 30 mm at the proximal end; and ii) a push rod dimensioned to be inserted into and reciprocally moved within the main body; and Step 920 to b) either 1) roll a menstrual receptacle into a spiral to form a rolled menstrual receptacle or 2) flatten a receptacle to form a compacted menstrual receptacle. The method further comprises Step 930 to c) at least partially insert the rolled menstrual receptacle or the compacted menstrual receptacle into the proximal end of the main body; Step 940 to d) insert a proximal end of the push rod into the distal end of the main body; and Step 950 to e) insert the proximal end of the main body containing the rolled menstrual receptacle or the compacted menstrual receptacle into a vaginal opening. Additionally, the method comprises Step 960 to f) push the push rod toward the proximal end of the main body until the proximal end of the push rod pushes the rolled menstrual receptacle or the compacted menstrual receptacle into the vaginal opening. In many embodiments, the method also comprises Step 970 to optionally remove the main body from the vaginal opening after step f).

Various non-limiting exemplary embodiments according to the present disclosure are provided below.

EXEMPLARY EMBODIMENTS

In a first embodiment, the present disclosure provides a menstrual receptacle applicator. The menstrual receptacle applicator comprises a hollow cylindrical main body defining an open proximal end and an open distal end, the main body having an inner diameter of 16 millimeters (mm) to 30 mm at the proximal end and configured to house at least a portion of a menstrual receptacle. The menstrual receptacle applicator further comprises a push rod dimensioned to be inserted into and reciprocally moved within the main body.

In a second embodiment, the present disclosure provides a menstrual receptacle applicator according to the first embodiment, further comprising a cap dimensioned to receive the main body and engage with the push rod when the push rod is fully inserted into the main body.

In a third embodiment, the present disclosure provides a menstrual receptacle applicator according to the first embodiment or the second embodiment, wherein an outer diameter of the distal end of the main body is larger than an outer diameter of the proximal end of the main body.

In a fourth embodiment, the present disclosure provides a menstrual receptacle applicator according to any of the first through third embodiments, further comprising a friction fit between a portion of the push rod and a portion of the main body.

In a fifth embodiment, the present disclosure provides a menstrual receptacle applicator according to the fourth embodiment, wherein the friction fit is provided by at least one protrusion disposed on an exterior surface of the push rod, at least one protrusion disposed on an interior surface of the main body, a clasp formed between a portion of the main body and the push rod, a piece of rubber disposed on the interior surface of the main body, a piece of rubber disposed on the exterior surface of the push rod, or any combination thereof.

In a sixth embodiment, the present disclosure provides a menstrual receptacle applicator according to any of the first through fifth embodiments, wherein the main body is formed of a cylindrical wall, the push rod is hollow and formed of a cylindrical wall, and the cylindrical wall of at least a portion of the push rod is thicker than the cylindrical wall of the main body.

In a seventh embodiment, the present disclosure provides a menstrual receptacle applicator according to the sixth embodiment, wherein the cylindrical wall of the push rod has a thickness of 1 millimeter (mm) to 10 mm.

In an eighth embodiment, the present disclosure provides a menstrual receptacle applicator according to any of the first through seventh embodiments, wherein the push rod further comprises a ledge formed at a proximal end.

In a ninth embodiment, the present disclosure provides a menstrual receptacle applicator according to any of the first through eighth embodiments, wherein the main body has an inner diameter of 18 mm to 28 mm at the proximal end.

In a tenth embodiment, the present disclosure provides a menstrual receptacle applicator according to any of the first through ninth embodiments, formed of plastic, wood, metal, or a combination thereof.

In an eleventh embodiment, the present disclosure provides a menstrual receptacle applicator according to any of the first through tenth embodiments, wherein the proximal end of the main body is free of any flanges formed thereon.

In a twelfth embodiment, the present disclosure provides a menstrual receptacle applicator according to any of the first through eleventh embodiments, wherein the proximal end of the push rod comprises a tapered shape.

In a thirteenth embodiment, the present disclosure provides a menstrual receptacle applicator according to any of the first through twelfth embodiments, wherein the proximal end of the main body is configured to house at least a portion of a rolled menstrual cup.

In a fourteenth embodiment, the present disclosure provides a menstrual receptacle applicator according to the thirteenth embodiment, wherein the proximal end is configured to house at least a portion of a rolled menstrual cup that has an outer diameter of 35 mm to 55 mm when not rolled.

In a fifteenth embodiment, the present disclosure provides a menstrual receptacle applicator according to any of the first through fourteenth embodiments, wherein the proximal end of the main body is configured to house at least a portion of a compacted menstrual disc.

In a sixteenth embodiment, the present disclosure provides a kit. The kit comprises one or more menstrual receptacles; and the menstrual receptacle applicator according to any of the first through fifteenth embodiments.

In a seventeenth embodiment, the present disclosure provides a kit according to the sixteenth embodiment, wherein the one or more menstrual receptacles comprise a menstrual cup.

In an eighteenth embodiment, the present disclosure provides a kit according to the sixteenth embodiment or the seventeenth embodiment, wherein the one or more menstrual receptacles comprise a menstrual disc.

In a nineteenth embodiment, the present disclosure provides a kit according to any of the sixteenth through eighteenth embodiments, further comprising a cap dimensioned to receive the main body and engage with the push rod when the push rod is fully inserted into the main body.

In a twentieth embodiment, the present disclosure provides a method of inserting a menstrual receptacle. The method comprises a) obtaining a menstrual receptacle applicator; either 1) rolling a menstrual receptacle into a spiral to form a rolled menstrual receptacle or 2) flattening a receptacle to form a compacted menstrual receptacle; and b) at least partially inserting the rolled menstrual receptacle or the compacted menstrual receptacle into the proximal end of the main body. The method further comprises c) inserting a proximal end of the push rod into the distal end of the main body; d) inserting the proximal end of the main body containing the rolled menstrual receptacle or the compacted menstrual receptacle into a vaginal opening; and e) pushing the push rod toward the proximal end of the main body until the proximal end of the push rod pushes the rolled menstrual receptacle or the compacted menstrual receptacle into the vaginal opening. The menstrual receptacle applicator comprises a hollow cylindrical main body defining an open proximal end and an open distal end, the main body having an inner diameter of 16 millimeters (mm) to 30 mm at the proximal end; and a push rod dimensioned to be inserted into and reciprocally moved within the main body.

In a twenty-first embodiment, the present disclosure provides a method according to the twentieth embodiment, further comprising removing the main body from the vaginal opening after step f).

In a twenty-second embodiment, the present disclosure provides a method according to the twentieth embodiment or the twenty-first embodiment, wherein step d) is performed before step c).

In a twenty-third embodiment, the present disclosure provides a method according to the twentieth embodiment or the twenty-first embodiment, wherein step e) is performed before step d).

In a twenty-fourth embodiment, the present disclosure provides a method according to any of the twentieth through twenty-third embodiments, wherein the menstrual receptacle is a menstrual cup.

In a twenty-fifth embodiment, the present disclosure provides a method according to any of the twentieth through twenty-third embodiments, wherein the menstrual receptacle is a menstrual disc.

In a twenty-sixth embodiment, the present disclosure provides a method according to the twenty-fifth embodiment, wherein the rolled menstrual receptacle or the compacted menstrual disc is partially inserted into the proximal end of the main body and a portion of the menstrual cup or the menstrual disc protrudes from the proximal end of the main body.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A menstrual receptacle applicator for inserting a menstrual receptacle, the menstrual receptacle applicator comprising:

a) a hollow cylindrical main body defining an open proximal end and an open distal end, the open proximal end having an inner diameter of 16 millimeters (mm) to 30 mm and configured such that at least a portion of a menstrual receptacle is insertable into the main body via the proximal end; and b) a push rod dimensioned to be inserted into the distal end of the main body and reciprocally moved within the main body.

2. The menstrual receptacle applicator of claim 1, further comprising a cap dimensioned to receive the main body and engage with the push rod when the push rod is fully inserted into the main body.

3. The menstrual receptacle applicator of claim 1, wherein an outer diameter of the distal end of the main body is larger than an outer diameter of the proximal end of the main body.

4. The menstrual receptacle applicator of claim 1, further comprising a friction fit between a portion of the push rod and a portion of the main body.

5. The menstrual receptacle applicator of claim 4, wherein the friction fit is provided by at least one protrusion disposed on an exterior surface of the push rod, at least one protrusion disposed on an interior surface of the main body, a clasp formed between a portion of the main body and the push rod, a piece of rubber disposed on the interior surface of the main body, a piece of rubber disposed on the exterior surface of the push rod, or any combination thereof.

6. The menstrual receptacle applicator of claim 1, wherein the main body is formed of a cylindrical wall, the push rod is hollow and formed of a cylindrical wall, and the cylindrical wall of at least a portion of the push rod is thicker than the cylindrical wall of the main body.

7. The menstrual receptacle applicator of claim 6, wherein the cylindrical wall of the push rod has a thickness of 1 millimeter (mm) to 10 mm.

8. The menstrual receptacle applicator of claim 1, wherein the push rod further comprises a ledge formed at a proximal end.

9. The menstrual receptacle applicator of claim 1, wherein the proximal end of the main body is free of any flanges formed thereon.

10. The menstrual receptacle applicator of claim 1, wherein the proximal end of the push rod comprises a tapered shape.

11. The menstrual receptacle applicator of claim 1, wherein the proximal end of the main body is configured such that at least a portion of a rolled menstrual cup is insertable into the main body via the proximal end.

12. The menstrual receptacle applicator of claim 11, wherein the proximal end is configured such that at least a portion of a rolled menstrual cup that has an outer diameter of 35 mm to 55 mm when not rolled is insertable into the main body via the proximal end.

13. The menstrual receptacle applicator of claim 1, wherein the proximal end of the main body is configured such that at least a portion of a compacted menstrual disc is insertable into the main body via the proximal end.

14. A kit comprising:

a) one or more menstrual receptacles; and b) the menstrual receptacle applicator of claim 1.

15. The kit of claim 14, wherein the one or more menstrual receptacles comprise a menstrual cup, a menstrual disc, or both.

16. The kit of claim 14, further comprising a cap dimensioned to receive the main body and engage with the push rod when the push rod is fully inserted into the main body.

* * * * *